United States Patent
Li et al.

(10) Patent No.: US 7,292,675 B1
(45) Date of Patent: Nov. 6, 2007

(54) AUTOMATIC PROTOCOL ASSISTANCE METHODS AND APPARATUS

(75) Inventors: Baojun Li, Waukesha, WI (US); Stephen Wayne Metz, Greenfield, WI (US); Rowland Frederick Saunders, Hartland, WI (US); Yaxi Shen, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/489,174

(22) Filed: Jul. 19, 2006

(51) Int. Cl.
H05G 1/54 (2006.01)

(52) U.S. Cl. .................... 378/116; 378/117; 378/21

(58) Field of Classification Search ............ 378/21–27, 378/101–118
See application file for complete search history.

(56) References Cited

U.S. PATENT DOCUMENTS

| 4,454,606 A | 6/1984 | Relihan | 378/97 |
| 6,192,105 B1 | 2/2001 | Hunter et al. | 378/108 |
| 6,944,266 B2 | 9/2005 | Yamazaki et al. | 378/98.7 |
| 2006/0262904 A1* | 11/2006 | Mertelmeier | 378/62 |

OTHER PUBLICATIONS

Author: Shramchenko et al.; Title: Optimized exposure control in digital mammography, Date: 2004; pp. 2: Proceedings of SPIE—vol. 5368; Medical Imaging 2004: Physics of Medical Imaging.

* cited by examiner

*Primary Examiner*—Jurie Yun
(74) *Attorney, Agent, or Firm*—Fisher Patent Group, LLC; Thomas M. Fisher

(57) ABSTRACT

A method of providing an automatic protocol assistance includes determining a number of exposures for a scan of an object, acquiring a low dose AEC exposure of the object or acquiring at least one of a PA and an AP view, calculating an initial technique, and automatically determining whether to use the initial technique to perform the scan or to not perform the scan.

20 Claims, 2 Drawing Sheets

AUTOMATIC PROTOCOL ASSISTANCE METHODS AND APPARATUS

BACKGROUND OF THE INVENTION

This invention relates generally to x-ray methods and apparatus, and more particularly to methods and apparatus that provide Automatic Protocol Assistance.

In x-ray tomosynthesis, a series of low dose x-ray images is acquired over a range of x-ray beam orientations relative to an imaged object. This viewing of the object from different orientations allows depth information to be incorporated into the final image. This depth information is, of course, unavailable in conventional (projection) x-ray imaging.

A typical range of the number of projections acquired during a tomosynthesis exam is between 41-61, at a frame rate of up to 6 fps. The tissue thickness along the x-ray path varies significantly at different angles, and there is a great risk of exposure cut-off in Automatic Exposure Control (AEC) mode. If this happens, the image quality will be compromised. Therefore, tomosynthesis typically utilizes exposures in fixed mode.

However, fixed-mode exposure poses a workflow issue. To ensure consistent image quality from patient to patient, acquisition technique should be adjusted based on various patient thickness. Otherwise, under-exposure or over-exposure are likely to occur. The former will suffer from poor image quality while the latter risks over-exposing patients. But estimating the proper technique for different patients is a quite challenging task. The technologists today in US represent a large body of variations in terms of experience levels. Sometimes with some technologists with less experience, retakes are taken for single energy chest x-ray. For tomosynthesis, it may be that retakes will increase. So to minimize the dependency on technologist's experience when selecting the technique for patients seems to be an effective strategy for manufacturers, such as Automatic Exposure Control (AEC) by GE Healthcare of Wisconsin. However, as stated above, there is a great risk of exposure cut-off in AEC mode.

Therefore it is desirable to addresses this workflow issue by developing methods and apparatus to automatically provide protocol assistance to help to achieve the optimized technique for different patients.

BRIEF DESCRIPTION OF THE INVENTION

In one aspect, a method of providing an automatic protocol assistance is provided. The method includes determining a number of exposures for a scan of an object, acquiring a low dose AEC exposure of the object or acquiring at least one of a PA and an AP view, calculating an initial technique, and automatically determining whether to use the initial technique to perform the scan or to not perform the scan.

In another aspect, a system includes an x-ray source, an x-ray detector positioned to receive x-rays emitted from the source, and a computer operationally coupled to the source and the detector. The computer is configured to determine a number of exposures for a scan of an object, acquire a low dose AEC exposure of the object or acquire at least one of a PA and an AP view, calculate an initial technique, and determine whether to use the initial technique to perform the scan or to not perform the scan.

In yet another aspect, a computer readable medium is provided that is embedded with a program that is configured to instruct a computer to determine a number of exposures for a scan of an object, acquire a low dose AEC exposure of the object or acquire at least one of a PA and an AP view, calculate an initial technique, and determine whether to use the initial technique to perform the scan or to not perform the scan.

DETAILED DESCRIPTION OF THE INVENTION

There are herein described methods and apparatus useful for imaging systems such as, for example, but not limited to an x-ray tomosynthesis system. The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention. Although, described in the setting of an x-ray tomosynthesis system, it is contemplated that the benefits of the invention accrue to all systems with x-ray sources.

Figure 1:
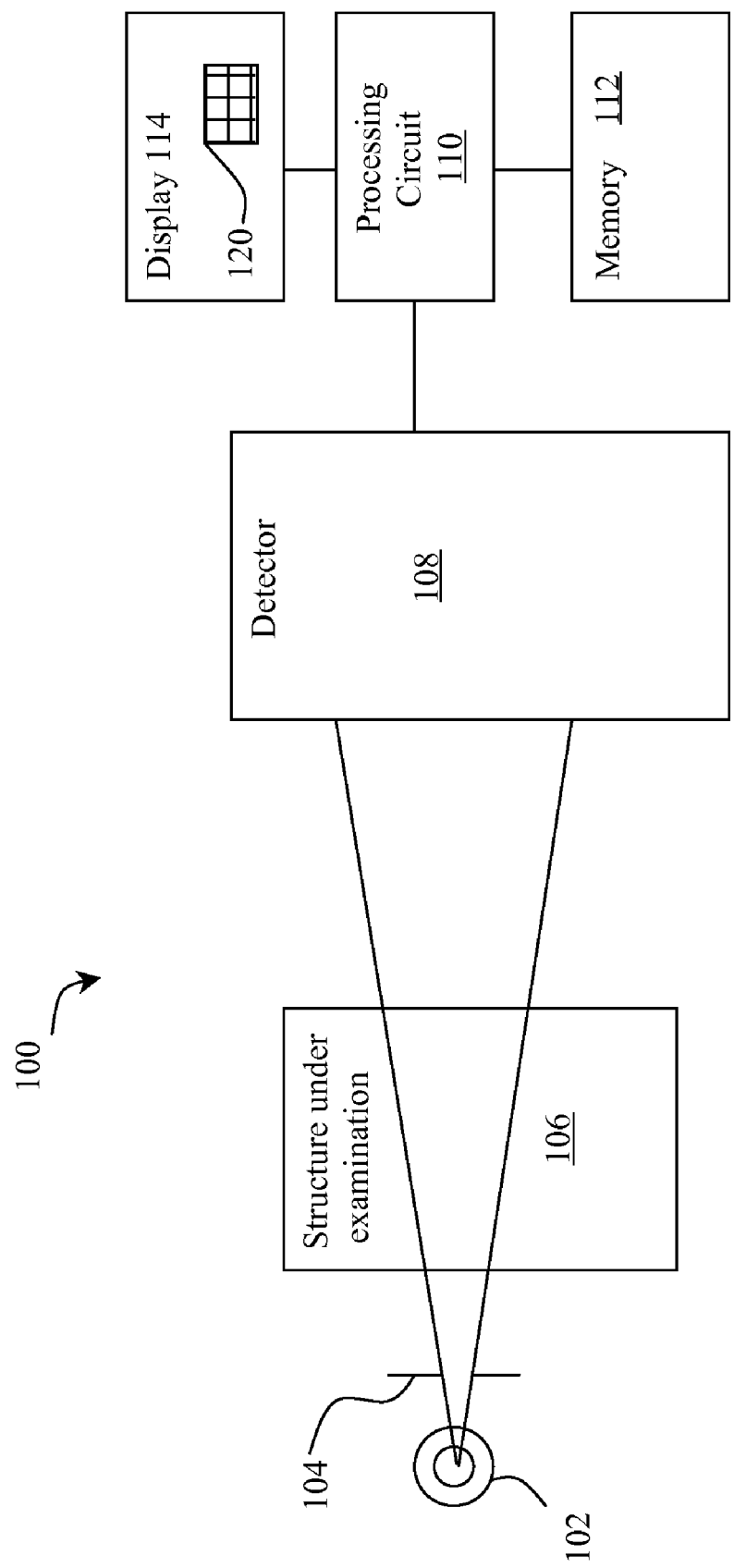
FIG. 1 illustrates an exemplary x-ray imaging system.

FIG. 1 illustrates an exemplary x-ray tomosynthesis imaging system 100. The imaging system 100 includes an x-ray source 102 and a collimator 104, which subject the structure under examination 106 to x-ray photons. As examples, the x-ray source 102 may be an x-ray tube, and the structure under examination 106 may be a human patient, test phantom or other inanimate object under test.

The x-ray imaging system 100 also includes a detector 108 coupled to a processing circuit 110. The processing circuit 110 (e.g., a microcontroller, microprocessor, custom ASIC, or the like) is coupled to a memory 112 and a display device 114. The memory 112 (e.g., including one or more of a floppy disk drive, CD-ROM drive, DVD drive, magnetic optical disk (MOD) device, or any other digital device including a network connecting device such as an Ethernet device for reading instructions and/or data from a computer-readable medium, such as a floppy disk, or an other digital source such as a network or the Internet, as well as yet to be developed digital means, and the like) stores imaging data.

Memory 112 may also store a computer program including instructions executed by the processing circuit 110 to implement the functions described herein. Processing circuit 110 provides an image 120 for display on device 114. As described in further detail herein, the image 120 may representative of different structures (e.g., soft-tissue, bone). The detector 108 may be a flat panel solid state image detector, for example, although conventional film images stored in digital form in the memory 112 may also be processed. In one embodiment, processing circuit 110 executes instructions stored in firmware (not shown). Generally, a processor is programmed to execute the processes described below.

Of course, the methods described herein are not limited to practice in system 100 and can be utilized in connection with many other types and variations of imaging systems. In one embodiment, processing circuit 110 is a computer that is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits. Although the herein described methods are described in a human patient setting, it is contemplated that the benefits of the invention accrue to non-human imaging systems such as those systems typically employed in small animal research.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also, as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

Although the herein described methods are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

Figure 2:
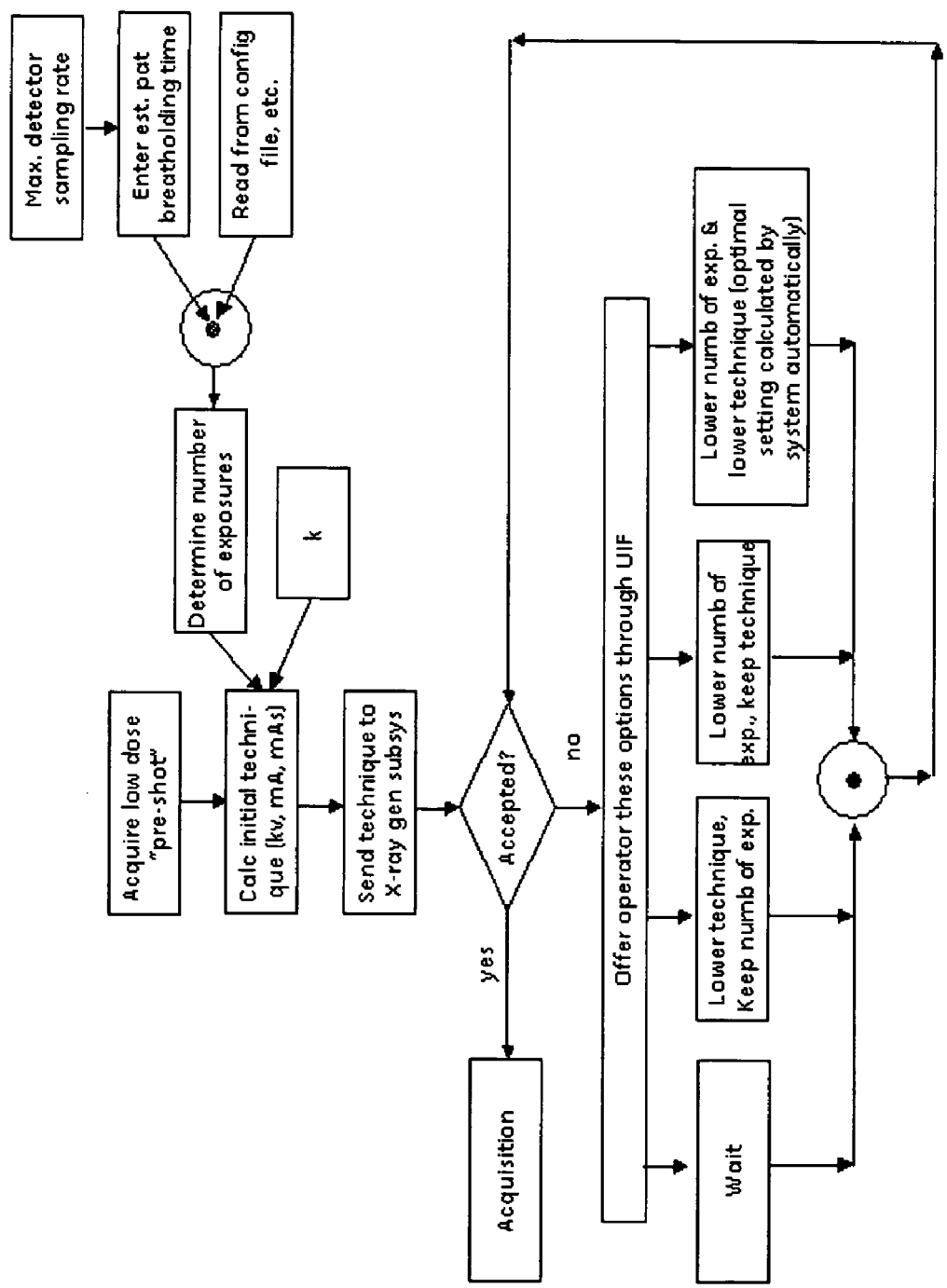
FIG. 2 illustrates workflow.

The method and algorithm for automatic protocol assistance has the following steps (see FIG. 2), in accordance with one embodiment:

1. Determine the number of exposures. There are two ways to do this:
   a. In one embodiment, the operator enters how long the exam time is (such as based on how long the patent can hold his/her breath time). In another embodiment, the operator enters how long the patient can hold his/her breath time (s), and the system automatically calculates the maximal number-of-exposures based on the detector sampling rate (frames per second, or fps):

number of exposures=patient breatholding time(s)/ detector sampling rate(fps)  (1)

b. Predetermined the number of exposures (stored in system configure file, etc.).

2. Acquire a low-dose AEC exposure of the patient ("pre-shot"). Alternatively the PA (posterior/anterior) or AP (anterior/posterior) view can be used for diagnosis, in which case the exposure used would be the nominal for that anatomical view and patient size.

3. Calculate the initial technique based on the pre-shot. The calculation could (but doesn't have to) use the following formula:

optimal technique per exposure(mAs)=$AEC$ exposure technique(mAs)*$k$/number-of-exposures  (2)

Where k is a configurable factor that may be fine-tuned for application or anatomy/view. K may be derived from prior knowledge database and total patient dose requirement.

4. Communicate the initial technique to the x-ray generation subsystem (e.g., generator, tube, etc.).

5. If the x-ray generation subsystem accepts the initial technique, then proceed and energize the x-ray source to acquire data.

6. If the x-ray generation subsystem rejects the initial technique, offers the following options to the operator to decide through an user interface:

a. Wait for x-ray generation subsystem to recover from its thermal condition (i.e., tube too hot, etc.);
   b. Suggest lower mAs per exposure, which the x-ray generation subsystem would accept under current situation, but keep the number of exposures;
   c. Suggest less number of exposures, which the x-ray generation subsystem would accept under current situation, but keep the mAs per exposure;
   d. Suggest lower mAs per exposure and less number of exposures, which the x-ray generation subsystem would accept under current situation, through an automatic optimization algorithm based on real-time negotiation with the x-ray generation subsystem;

7. The system offers flexibility in the user interface for operator to make the choice listed above either on an exam-by-exam basis or by setting the default choice(s).

One technical effect is that the herein described methods and apparatus improve the workflow and image quality for digital tomosynthesis by minimizing the operator-by-operator variability through automatic protocol assistance.

Exemplary embodiments are described above in detail. The assemblies and methods are not limited to the specific embodiments described herein, but rather, components of each assembly and/or method may be utilized independently and separately from other components described herein.

While the invention has been described in terms of various specific embodiments, those skilled in the art will recognize that the invention can be practiced with modification within the spirit and scope of the claims.

What is claimed is:

1. A method of providing an automatic protocol assistance for digital tomosynthesis, said method comprising:
   determining a number of tomosynthesis exposures for a scan of an object;
   acquiring an automatic exposure control exposure of the object or acquiring at least one of a posterior/anterior (PA) and an anterior/posterior (AP) view;
   calculating an initial technique for each of the number of tomosynthesis exposures, wherein an x-ray source is at different orientations with respect to a detector, each initial technique comprising a set of parameters including at least one parameter that is a function of at least one of an incident angle and a distance between the source and the detector; and
   automatically determining whether to use the plurality of initial techniques to perform or to not perform the number of exposures by sending the plurality of initial techniques to an x-ray generation subsystem that can accept or reject the initial techniques.

2. A method in accordance with claim 1 further comprising prompting a user to change scan parameters when it was automatically determined not to perform the number of exposures.

3. A method in accordance with claim 1 further comprising waiting for a system recovery when it was automatically determined not to perform the number of exposures.

4. A method in accordance with claim 2 wherein said prompting comprises suggesting lower mAs per exposure than the initial technique, which the x-ray generation subsystem accepts under current situation, but keep the number of exposures as previously determined.

5. A method in accordance with claim 2 wherein said prompting comprises suggesting less number of exposures than previously determined, which the x-ray generation subsystem accepts under current situation, but keep the mAs per exposure as per the initial technique.

6. A method in accordance with claim 2 wherein said prompting comprises suggesting lower mAs per exposure than the initial technique and less number of exposures than determined, which the x-ray generation subsystem accepts under current situation, through an automatic optimization algorithm based on real-time negotiation with the x-ray generation subsystem.

7. A method in accordance with claim 4 wherein said prompting also comprises suggesting less number of exposures than previously determined, which the x-ray generation subsystem accepts under current situation, but keep the mAs per exposure as per the initial technique.

8. A method in accordance with claim 7 wherein said prompting also comprises suggesting lower mAs per exposure than the initial technique and less number of exposures than determined, which the x-ray generation subsystem accepts under current situation, through an automatic optimization algorithm based on real-time negotiation with the x-ray generation subsystem.

9. A system comprising:
   an x-ray source;
   an x-ray detector positioned to receive x-rays emitted from said source while said source is moved relative to said detector in a tomosynthesis scan; and
   a computer operationally coupled to said source and said detector, said computer configured to:
   determine a number of tomosynthesis exposures for a scan of an object;
   acquire an automatic exposure control exposure of the object or acquire at least one of a posterior/anterior (PA) and an anterior/posterior (AP) view;
   calculate an initial technique for each of the number of tomosynthesis exposures, wherein the x-ray source is at different orientations with respect to the detector, each initial technique comprising a set of parameters including at least one parameter that is a function of at least one of an incident angle and a distance from the x-ray source to the x-ray detector; and
   determine whether to use the plurality of initial techniques to perform or to not perform the number of exposures by sending the plurality of initial techniques to an x-ray generation subsystem that can accept or reject the plurality of initial techniques.

10. A system in accordance with claim 9, wherein said computer is configured to prompt a user to change scan parameters when it was determined not to perform the number of exposures.

11. A system in accordance with claim 9, wherein said computer is configured to wait for a system recovery when it was determined not to perform the number of exposures.

12. A system in accordance with claim 9, wherein said computer is configured to suggest lower mAs per exposure than the initial technique, which the x-ray generation subsystem accepts under current situation, but keep the number of exposures as previously determined.

13. A system in accordance with claim 9, wherein said computer is configured to suggest less number of exposures than previously determined, which the x-ray generation subsystem accepts under current situation, but keep the mAs per exposure as per the initial technique.

14. A system in accordance with claim 9, wherein said computer is configured to suggest lower mAs per exposure than the initial technique and less number of exposures than determined, which the x-ray generation subsystem accepts under current situation, through an automatic optimization algorithm based on real-time negotiation with the x-ray generation subsystem.

15. A system in accordance with claim 12, wherein said computer is configured to also suggest less number of exposures than previously determined, which the x-ray generation subsystem accepts under current situation, but keep the mAs per exposure as per the initial technique.

16. A system in accordance with claim 15 wherein said computer is configured to also suggest lower mAs per exposure than the initial technique and less number of exposures than determined, which the x-ray generation subsystem accepts under current situation, through an automatic optimization algorithm based on real-time negotiation with the x-ray generation subsystem.

17. A computer readable medium embedded with a program configured to instruct a computer to:
   determine a number of tomosynthesis exposures for a scan of an object;
   acquire an automatic exposure control exposure of the object or acquire at least one of a posterior/anterior (PA) and an anterior/posterior (AP) view;
   calculate an initial technique for each of the number of tomosynthesis exposures wherein an x-ray source is at different orientations with respect to a detector, each initial technique comprising a set of parameters including at least one parameter that is a function of an incident angle and a distance between the x-ray source and the x-ray detector; and
   determine whether to use the plurality of initial techniques to perform or to not perform the number of exposures by sending the plurality of initial techniques to an x-ray generation subsystem that can accept or reject the plurality of initial techniques.

18. A medium in accordance with claim 17, wherein said program is further configured to instruct the computer to prompt a user to change scan parameters when it was determined not to perform the number of exposures.

19. A medium in accordance with claim 17, wherein said program is further configured to instruct the computer to wait for a system recovery when it was automatically determined not to perform the number of exposures.

20. A medium in accordance with claim 17, wherein said program is further configured to instruct the computer to:
   suggest lower mAs per exposure than the initial technique, which an x-ray generation subsystem accepts under current situation, but keep the number of exposures as previously determined;
   suggest less number of exposures than previously determined, which the x-ray generation subsystem accepts under current situation, but keep the mAs per exposure as per the initial technique; and
   suggest lower mAs per exposure than the initial technique and less number of exposures then determined, which the x-ray generation subsystem accepts under current situation, through an automatic optimization algorithm based on real-time negotiation with the x-ray generation subsystem.

* * * * *